United States Patent [19]

Black et al.

[11] Patent Number: 5,464,845
[45] Date of Patent: Nov. 7, 1995

[54] METHODS FOR LOWERING SERUM CHOLESTEROL

[75] Inventors: Larry J. Black; Henry U. Bryant, both of Indianapolis; George J. Cullinan, Trafalgar; Raymond F. Kauffman, Carmel, all of Ind.

[73] Assignee: Eli Lilly and Company, Indianapolis, Ind.

[21] Appl. No.: 159,159

[22] Filed: Nov. 30, 1993

Related U.S. Application Data

[63] Continuation-in-part of Ser. No. 995,222, Dec. 22, 1992, abandoned.

[51] Int. Cl.⁶ .................. A61K 31/445; A61K 31/38; A61K 31/40; A61K 31/56
[52] U.S. Cl. ................. 514/326; 514/443; 514/422; 514/171
[58] Field of Search ................. 514/443, 326, 514/422, 171

[56] References Cited

U.S. PATENT DOCUMENTS

| | | | |
|---|---|---|---|
| 4,133,814 | 1/1979 | Jones et al. | 548/525 |
| 4,418,068 | 11/1983 | Jones | 514/337 |
| 4,729,999 | 3/1988 | Young | 514/239.5 |
| 4,894,373 | 1/1990 | Young | 514/239.2 |

OTHER PUBLICATIONS

U.S. application No. 07/920,933 Larry J. Black et al. filed on Jul. 28, 1992.
Williams, et al., *Journal of Bone and Mineral Research*, 6 (1991).
Jones, et al., *J. Med. Chem.*, 27, 1057–1066 (1984).
Feldman, et al., *Bone and Mineral*, 7, 245–254 (1989).
Williams, et al., *Bone and Mineral*, 14, 205–220 (1991).
Turner, et al., *J. Bone and Min. Res.*, 2, No. 5, 449–456 (1987).
Breckenridge, et al., *Lipids*, 22, No. 7, 505–512 (1987).
Lazier, et al., *Biochem. Cell Biol.*, 68, 210–217 (1990).
Lobo, *J. Clin. Endocrinol. Metab.*, 73, No. 5, 925–930 (1991).
Love, et al., *Ann. Intern. Med.*, 115, No. 11, 860–864 (1991).
Walsh, et al., *N. Engl. J. Med.*, 325, No. 17, 1196–1204 (1991).
Bagdade, et al., *J. Clin. Endocrinol. Metab.*, 70, No. 4, 1132–1135 (1990).
Love, et al., *J. Natl. Cancer Inst.*, 82, No. 16, 1327–1332 (1990).
Teo, et al., *J. Med. Chem.*, 35, 1330–1339 (1992).
Cypriani, et al., *J. Steroid Biochem.*, 31, No. 5, 763–771 (1988).
Cypriani, et al., "Effect of Estradiol and Antiestrogens on Cholesterol Synthesis in Hormone–Dependent and Independent Breast Cancer Cell Lines", *Biochem. Biophys. ACTA* 972 167–178 (1988).
Cypriani, et al., "Role of Estrogen Receptors and Antiestrogen Binding Sites in an Early Effect of Antiestrogens, the Inhibition of Cholesterol Biosynthesis", *Chem. Abstr.* 110: 6958v, (1989).
American Chemical Society *Registry*, RN #63676-25-5, 1993.

*Primary Examiner*—Raymond Henley, III
*Assistant Examiner*—William R. A. Jarvis
*Attorney, Agent, or Firm*—James J. Sales

[57] ABSTRACT

A method of lowering serum cholesterol levels comprising administering to a patient a serum cholesterol lowering amount of a compound having the formula

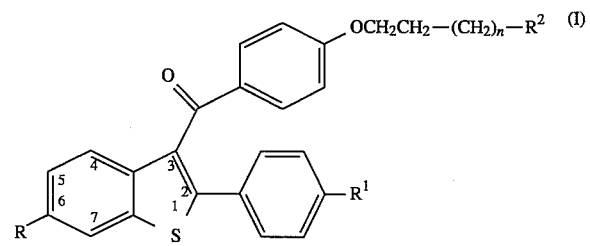

wherein
n is 0, 1 or 2;

R is hydroxyl, methoxy, $C_1$–$C_7$ alkanoyloxy, $C_3$–$C_7$ cycloalkanoyloxy, ($C_1$–$C_6$ alkoxy)-$C_1$–$C_7$ alkanoyloxy, substituted or unsubstituted aroyloxy, or substituted or unsubstituted aryloxycarbonyloxy;

$R^1$ is hydrogen, hydroxyl, chloro, bromo, methoxy, $C_1$–$C_7$ alkanoyloxy, $C_3$–$C_7$ cycloalkanoyloxy, ($C_1$–$C_6$ alkoxy)-$C_1$–$C_7$ alkanoyloxy, substituted or unsubstituted aroyloxy, or substituted or unsubstituted aryloxycarbonyloxy;

$R^2$ is a heterocyclic ring selected from the group consisting of pyrrolidino, piperidino, or hexamethyleneimino; or a pharmaceutically acceptable salt or solvate thereof.

22 Claims, No Drawings

METHODS FOR LOWERING SERUM CHOLESTEROL

CROSS REFERENCE TO RELATION APPLICATION

This application is a continuation-in-part of application Ser. No. 07/995,222, filed Dec. 22, 1992, now abandoned.

BACKGROUND OF THE INVENTION

The present invention relates to the discovery that a group of 2-phenyl-3-aroylbenzothiophenes are useful for lowering serum cholesterol.

All mammalian cells require cholesterol as a structural component of their cell membranes and for non-sterol end products. Cholesterol is also required for steroid hormone synthesis. The very property, however, that makes cholesterol useful in the cell membranes, its insolubility in water, also makes it potentially lethal. When cholesterol accumulates in the wrong place, for example within the wall of an artery, it cannot be readily mobilized and its presence leads to the development of an atherosclerotic plaque. Elevated concentrations of serum cholesterol associated with low density lipoproteins have been demonstrated to be a major contributing factor in the development and progression of atherosclerosis.

In mammals, serum lipoprotein is composed of cholesterol together with cholesteryl esters, triglycerides, phospholipids and apoproteins. Serum or plasma lipoprotein is comprised of several fractions. The major fractions or classes of plasma lipoproteins are very low density lipoprotein (VLDL), low density lipoprotein (LDL), intermediate density lipoprotein (IDL), and high density lipoprotein (HDL). These classes differ from one another in size, density and in the relative proportions of triglycerides and cholesteryl esters in the core, and in the nature of the apoproteins on the surface.

In mammals, serum cholesterol is derived from exogenous dietary sources as well as through endogenous synthesis. Endogenous synthesis of cholesterol involves a complex set of enzyme-catalyzed reactions and regulatory mechanisms generally termed the mevalonate pathway. Cells face a complex problem in regulating mevalonate synthesis because cholesterol, the bulk end product of mevalonate metabolism, is derived from plasma LDL which enters the cell by receptor-mediated endocytosis, as well as from synthesis within the cell. Each cell must balance these external and internal sources so as to sustain mevalonate synthesis while avoiding sterol over accumulation. This balance is achieved through feedback regulation of at least two sequential enzymes in mevalonate synthesis, 3-hydroxy-3-methylglutaryl coenzyme A (HMG-CoA) synthase and HMG-CoA reductase, and also of LDL receptors. In the absence of LDL, mammalian cells maintain high activities of the two enzymes, thereby synthesizing mevalonate for production of cholesterol as well as the non-sterol products. When LDL is present from exogenous sources, HMG-CoA synthase and reductase activity is repressed and the cells produce smaller amounts of mevalonate for the non-sterol end products.

Abundant evidence indicates that treatment of hyperlipoproteinemia may diminish or prevent atherosclerotic complications. In addition to a diet that maintains a normal body weight and minimizes concentrations of lipids in plasma, therapeutic strategies include elimination of factors that exacerbate hyperlipoproteinemia and the administration of therapeutic agents that lower plasma concentrations of lipoproteins, either by diminishing the production of lipoproteins or by enhancing the efficiency of their removal from plasma.

The most promising class of drugs currently available for the treatment of hypercholesterolemia act by inhibiting HMG-CoA reductase, the rate-limiting enzyme of endogenous cholesterol synthesis. Drugs of this class competitively inhibit the activity of the enzyme. Eventually, this lowers the endogenous synthesis of cholesterol and, by normal homeostatic mechanisms, plasma cholesterol is taken up by LDL receptors to restore the intracellular cholesterol balance.

Relative to other cells in the body, liver cells play a critical role in maintaining serum cholesterol homeostasis by both releasing precursors of LDL and through receptor-mediated LDL uptake from the serum. In both man and animal models an inverse correlation appears to exist between liver LDL receptors and LDL-associated serum cholesterol levels. In general, higher hepatocyte receptor numbers result in lower LDL-associated serum cholesterol levels. Cholesterol released into hepatocytes can be stored as cholesterol esters, converted into bile acids and released into the bile duct, or enter into an oxycholesterol pool. It is this oxychotesterol pool that is believed to be involved in end product repression of both the genes of the LDL receptor and enzymes involved in the cholesterol synthetic pathway.

Transcription of the LDL receptor gene is known to be repressed when cells have an excess supply of cholesterol, probably in the form of oxycholesterol. A DNA sequence in the LDL receptor promoter region, known as the sterol response element, appears to confer this sterol end product repression. This element has been extensively studied (Brown, Goldstein and Russell, U.S. Pat. Nos. 4,745,060 and 4,935,363) and appears to consist of a 16 base pair sequence that occurs 5' of the LDL receptor coding region. The sterol response element can be inserted into genes that normally do not respond to cholesterol, conferring sterol end product repression on the chimeric gene. The exact mechanism of this repression is not understood. There is, however, abundant evidence that polar intermediates in cholesterol biosynthesis and naturally occurring as well as synthetic hydroxysterols repress genes containing the sterol response element.

It has been suggested that a hydroxycholesterol binding protein serves as a receptor. When the receptor is bound to an oxysterol it acts on the sterol response element to control transcription through a mechanism that is similar to the action of members of the steroid hormone receptor super gene family.

In populations where coronary heart disease is a major health problem, the incidence of the disease is markedly lower in women than in men. This difference is particularly true in younger age groups, such as men and women between 35 and 44 years of age.

Generally, plasma lipoprotein metabolism is influenced by the circulating concentrations of gonadal steroids. Changes in serum estrogen and androgen concentrations, resulting from alterations in gonadal status or from the administration of exogenous gonadal steroids, are associated with changes in serum lipoprotein levels. The changes effected by estrogens and androgens generally support the proposition that sex differences in lipoproteins are due to hormonal differences between men and women.

The generally accepted relationship between gonadal steroids and plasma lipoproteins is that androgens lower HDL concentrations and increase LDL, thus contributing to the low HDL and high LDL levels observed in men when compared to women. Estrogens are held to have opposite effects on lipoproteins; that is, HDL is raised and LDL is lowered. These sex steroid-induced differences in lipoprotein concentrations are thought to contribute to the lower incidence of cardiovascular disease in women compared to men. After menopause, the protective effect of estrogens in women is lost and the incidence of cardiovascular disease increases towards the male levels. Postmenopausal women who take estrogens generally have lower rates of cardiovascular disease than women of a similar age who do not. Estrogen, particularly when taken orally, lowers plasma levels of LDL and raises those of HDL.

The mechanisms by which estrogen lowers levels of LDL and raises those of HDL are not known. In general, changes in the plasma concentration of a lipoprotein result from changes in the rate of its synthesis or the rate of its catabolism. For example, estrogen may lower LDL levels by increasing the clearance of LDL from plasma, since estrogen increases the number of hepatic LDL receptors in animals.

Although estrogens have beneficial effects on serum LDL, long-term estrogen therapy has been implicated in a variety of disorders, including an increase in the risk of uterine cancer and possibly breast cancer, causing many women to avoid this treatment. Recently suggested therapeutic regimens which seek to lessen the cancer risk, such as administering combinations of progestogen and estrogen, cause the patient to experience unacceptable bleeding. Furthermore, combining progesterone with estrogen seems to blunt the serum cholesterol lowering effects of estrogen. The significant undesirable effects associated with estrogen therapy support the need to develop alternative therapies for hypercholesterolemia that have the desirable effects on serum LDL but do not cause undesirable side effects.

Attempts to fill this need by the use of compounds commonly known as antiestrogens, which interact with the estrogen receptor and/or bind what has been termed the antiestrogen binding site (AEBS), have had limited success, perhaps due to the fact that these compounds generally display a mixed agonist/antagonist effect. That is, although these compounds can antagonize estrogen interaction with the receptor, the compounds themselves may cause estrogenic responses in those tissues having estrogen receptors such as the uterus. Therefore, some antiestrogens, such as tamoxifen, are subject to the same adverse effects associated with estrogen therapy.

The current invention provides methods for lowering serum LDL levels without the associated adverse effects of estrogen therapy, and thus provides an effective and acceptable treatment for hypercholesterolemia.

The 2-phenyl-3-aroylbenzothiophene compounds of formula I that are the active component in the methods of this invention were in a group of compounds developed by C. David Jones and Tulio Suarez as anti-fertility agents (see U.S. Pat. No. 4,133,814, issued Jan. 9, 1979). Certain compounds in the group were found to be useful in suppressing the growth of mammary tumors.

Jones later found a group of those compounds, including the formula I compounds, to be useful for antiestrogen and antiandrogen therapy, especially in the treatment of mammary and prostatic tumors (see U.S. Pat. No. 4,418,068, issued Nov. 29, 1983). One of these compounds, the compound of formula I wherein n is O, R and $R^1$ are hydroxyl, and $R^2$ is a piperidino ring, was clinically tested for a brief time for the treatment of breast cancer. That compound is called raloxifene (formerly called keoxifene).

SUMMARY OF THE INVENTION

This invention provides a new method for lowering serum cholesterol levels, comprising administering to a patient a serum cholesterol lowering amount of a compound of formula I

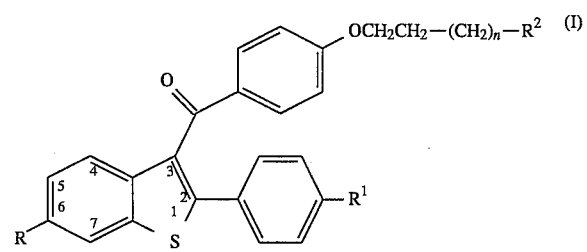

wherein n is 0, 1 or 2;

R is hydroxyl, methoxy, $C_1$–$C_7$ alkanoyloxy, $C_3$–$C_7$ cycloalkanoyloxy, ($C_1$–$C_6$ alkoxy)-$C_1$–$C_7$ alkanoyloxy, substituted or unsubstituted aroyloxy, or substituted or unsubstituted aryloxycarbonyloxy;

$R^1$ is hydrogen, hydroxyl, halo, methoxy, $C_1$–$C_7$ alkanoyloxy, $C_3$–$C_7$ cycloalkanoyloxy, ($C_1$–$C_6$ alkoxy)-$C_1$–$C_7$ alkanoyloxy, substituted or unsubstituted aroyloxy, or substituted or unsubstituted aryloxycarbonyloxy;

$R^2$ is a heterocyclic ring selected from the group consisting of pyrrolidino, piperidino, or hexamethyleneimino; or a pharmaceutically acceptable salt or solvate thereof.

DETAILED DESCRIPTION OF THE INVENTION

The general chemical terms used in the description of a compound of formula I have their usual meanings. For example, the term "alkyl" by itself or as part of another substituent means a straight or branched chain alkyl radical having the stated number of carbon atoms such as methyl, ethyl, propyl, and isopropyl and higher homologues and isomers where indicated.

The term "alkoxy" means an alkyl group having the stated number of carbon atoms linked by an oxygen atom, such as methoxy, ethoxy, propoxy, butoxy, pentyloxy, and hexyloxy and also includes branched chain structures such as, for example, isopropoxy and isobutoxy.

The term "$C_1$–$C_7$-alkanoyloxy" means a group —O—C(O)—$R^a$ where $R^a$ is hydrogen or $C_1$–$C_6$ alkyl and includes formyloxy, acetoxy, propanoyloxy, butanoyloxy, pentanoyloxy, hexanoyloxy, and the like and also includes branched chain isomers such as, for example, 2,2-dimethylpropanoyloxy, and 3,3-dimethylbutanoyloxy.

Analogously, the term "$C_4$–$C_7$ cycloalkanoyloxy" means a group —O—C(O)—($C_3$–$C_6$ cycloalkyl) where the $C_3$–$C_6$ alkyl group includes cyclopropyl, cyclobutyl, cyclopentyl and cyclohexyl.

The term "($C_1$–$C_6$-alkoxy)-$C_1$–$C_7$-alkanoyloxy" means a group —O—C(O)—$R^b$—O—($C_1$–$C_6$ alkyl) where $R^b$ is a bond ($C_1$–$C_6$ alkoxycarbonyloxy) or $C_1$–$C_6$ alkanediyl and includes, for example, methoxycarbonyloxy, ethoxycarbonyloxy, propoxycarbonyloxy, butoxycarbonyloxy, methoxyacetoxy, methoxypropanoyloxy, methoxybutanoyloxy, methoxy-pentanoyloxy, methoxyhexanoyloxy, ethoxyacetoxy, ethoxypropanoyloxy, ethoxybutanoyloxy, ethoxypentanoyloxy, ethoxyhexanoyloxy, propoxyacetoxy, propoxypropanoyloxy, propoxybutanoyloxy, and the like.

The term "unsubstituted or substituted aroyloxy" means a group —O—C(O)-aryl where aryl is a phenyl, naphthyl, thienyl or furyl group that is, as to each group, unsubstituted or monosubstituted with a hydroxyl, halo, $C_1$–$C_3$ alkyl, or $C_1$–$C_3$ alkoxy substituent.

The term "unsubstituted or substituted aryloxycarbonyloxy" means a group —O—C(O)—O-aryl where aryl is a phenyl, naphthyl, thienyl or furyl group that is, as to each group, unsubstituted or monosubstituted with a hydroxyl, halo, $C_1$–$C_3$ alkyl or $C_1$–$C_3$ alkoxy substituent.

The term "halo" means chloro, fluoro, bromo or iodo.

The compounds of formula I can be named either using methanone as the molecular skeleton or using benzo[b]thiophene as the molecular skeleton. For illustrative purposes, compounds of formula I are named infra using one or both molecular skeletons.

The current invention concerns the discovery that a select group of 2-phenyl-3-aroylbenzothiophenes (benzothiophenes), the compounds of formula I, are useful for lowering serum cholesterol levels. The methods of treatment provided by this invention comprise administering to a patient a serum lipid lowering amount of a compound of formula I, or a pharmaceutically acceptable acid addition salt or solvate thereof. The present method includes both medical therapeutic and/or prophylactic treatment, as appropriate. Generally, the compound is formulated with common excipients, diluents or carriers, and compressed into tablets, or formulated as elixirs or solutions for convenient oral administration, or administered by the intramuscular or intravenous routes. The compounds can be administered transdermally, and are well suited to formulation as sustained release dosage forms and the like.

The benzothiophenes of formula I lower serum cholesterol levels in animals and should be particularly useful for lowering serum cholesterol levels in humans. Excess serum cholesterol may result from a variety of conditions and disorders, including a lack of endogenous estrogen such as occurs in women following cessation of menstruation due to natural, surgical, or other processes, and patients having gonadal dysgenesis.

The benzothiophenes of formula I are a series of nonsteroidal compounds that exhibit high affinity for conventional estrogen receptors in primary sex target tissues. However, they elicit minimal estrogenic responses in those tissues, and actually serve as potent antagonists of natural estrogens such as estradiol. In contrast to other structurally distinct antiestrogen compounds, the benzothiophenes of formula I are able to antagonize classical estrogenic responses in primary sex target tissues while eliciting an estrogenic response on serum cholesterol levels. This dichotomy indicates selective agonist/antagonist actions on specific target cells which are highly desirable in treating hypercholesterolemia. Accordingly, a primary benefit of the current discovery is that the benzothiophenes of formula I lower serum cholesterol levels but do not elicit significant estrogenic responses in the primary sex target tissues. Thus, the current invention provides a method of lowering serum cholesterol levels, comprising administering to a patient an amount of a compound of formula I that lowers serum LDL levels but does not significantly affect the primary sex target tissues. This combination of features allows for long-term treatment of the chronic ailment with little risk of developing the undesirable effects of customary estrogen replacement therapy.

The biological action of the benzothiophenes of formula I is complex and may be unrelated to the detectable presence of the parent compound in the blood. Following oral administration of a preferred benzothiophene of this invention, raloxifene (administered as the hydrochloride), to human subjects in the clinic, the parent compound was not detected in the serum of those subjects. It was determined that following oral administration, the compound was extensively conjugated to the glucuronidated form. Although no biological endpoints were measured in the human recipients, there was concern that the compound was not bioavailable.

Experiments were undertaken to address the bioavailability issue in laboratory animals where biological activity could be assessed. The animal studies indicated that raloxifene was maximally active in inhibiting both uterine uptake of tritiated-estradiol and the normal uterotrophic response to estradiol even under conditions where raloxifene was extensively conjugated in the plasma of the animals. Moreover, the conjugate, isolated from the urine of human subjects treated with raloxifene, displayed significant antiestrogenic/antiuterotrophic activity when administered intravenously to rats, and inhibited the interaction of tritiated-estradiol with rat uterine estrogen receptors in a manner similar to the parent compound at temperatures approaching physiologic conditions. Since the compounds did not bind at 4° C., these studies suggested the conjugated compound may have been converted to the parent form at the site of action, presumably by the action of β-glucuronidase. Such conversion may contribute to the activity of the compound. β-Glucuronidase is fairly ubiquitous and would presumably be available for converting the conjugated compound to the parental form if required for activity. Therefore, conjugation of the benzothiophenes of formula I is not considered to be necessarily detrimental to their bioavailability.

Thus, the method of treatment provided by this invention is practiced by administering to a patient an amount of a compound of formula I, or a pharmaceutically acceptable salt or solvate thereof, that is effective to lower serum cholesterol levels. A particular benefit of this method is that it avoids potentially harmful and unacceptable estrogenic side effects. The present method includes both medical therapeutic and/or prophylactic treatment, as appropriate.

The method also includes the administration of a compound of formula I and estrogen, either independently or in combination. The term estrogen as used herein refers to any compound which approximates the spectrum of activities of the naturally acting molecule which is commonly believed to be 17β-estradiol. Examples of such compounds include estriol, estrone, ethynyl estradiol, Premarin (a commercial preparation of conjugated estrogens isolated from natural sources-Ayerst), and the like. Again, due to the selective agonist/antagonist properties of the compounds of formula I, this combination provides the benefits of estrogen therapy without the concomitant adverse effects associated with estrogen therapy alone.

Preferred methods of this invention comprise the use of compounds of formula I wherein n is O; and R and $R^1$ are independently hydroxyl, $C_1$–$C_7$ alkanoyloxy, ($C_1$–$C_6$ alkoxy)-$C_1$–$C_7$ alkanoyloxy, unsubstituted or substituted benzoyloxy or unsubstituted or substituted phenoxycarbonyloxy. Further preferred methods include the use of formula I compounds wherein R and $R^1$ are the same. Certain $R^2$ groups also demonstrate preferable characteristics when used in the methods of this invention. For example, preferred methods of this invention include the use of formula I compounds wherein $R^2$ is piperidino or pyrrolidino. Especially preferred are those compounds where $R^2$ is piperidino or pyrrolidino and R and $R^1$ are hydroxyl. A most preferred formula I compound is raloxifene.

The formula I compounds and their salts can be made according to established procedures, such as those detailed in U.S. Pat. Nos. 4,133,814 and 4,418,068, both of which are incorporated by reference. In general, the process starts with a benzo[b]thiophene having a 6-hydroxyl group and a 2-(4-hydroxyphenyl) group. The starting compound is protected, alkylated, and deprotected to form the formula I compounds wherein R and $R^1$ are both hydroxy. The formula I compounds that are ethers, esters, and carbonates may then be formed if desired. Examples of the preparation of such compounds are provided in the U.S. patents discussed above. Specific preparations of other derivatized compounds useful in the current invention are described below. Modifications to the above methods may be necessary to accommodate reactive functionatities of particular substituents. Such modifications would be apparent to, or readily ascertained by, those skilled in the art.

The formula I compounds form acid and base addition salts with a wide variety of organic and inorganic acids and bases and include the physiologically acceptable salts which are often used in pharmaceutical chemistry. Such salts are also part of this invention. Typical inorganic acids used to form such salts include hydrochloric, hydrobromic, hydroiodic, nitric, sulfuric, phosphoric, hypophosphoric and the like. Salts derived from organic acids, such as aliphatic mono and dicarboxylic acids, phenyl-substituted alkanoic acids, hydroxyalkanoic and hydroxyalkandioic acids, aromatic acids, aliphatic and aromatic sulfonic acids, may also be used. Typical salts include acetate, phenylacetate, trifluoroacetate, acrylate, ascorbate, benzoate, chlorobenzoate, dinitrobenzoate, hydroxybenzoate, methoxybenzoate, methylbenzoate, o-acetoxybenzoate, naphthalene-2-benzoate, bromide, isobutyrate, phenylbutyrate, β-hydroxybutyrate, butyne-1,4-dioate, hexyne-1,4-dioate, caprate, caprylate, chloride, cinnamate, citrate, formate, fumarate, glycollate, heptanoate, hippurate, lactate, malate, maleate, hydroxymaleate, malonate, mandelate, mesylate, nicotinate, isonicotinate, nitrate, oxalate, phthalate, teraphthalate, phosphate, monohydrogenphosphate, dihydrogenphosphate, metaphosphate, pyrophosphate, propiolate, propionate, phenylpropionate, salicylate, sebacate, succinate, subcrate, sulfate, bisulfate, pyrosulfate, sulfite, bisulfite, sulfonate, benzenesulfonate, p-bromophenylsulfonate, chlorobenzenesulfonate, ethanesulfonate, 2-hydroxyethanesulfonate, methane-sulfonate, naphthalene-1-sulfonate, naphthalene-2-sulfonate, p-toluenesulfonate, xylenesulfonate, tartrate, and the like.

In addition, some of the formula I compounds may form solvates with water or organic solvents such as ethanol. These solvates are also contemplated for use in the methods of this invention.

The acid addition salts are typically formed by reacting a compound of formula I with an equimolar or excess amount of acid. The reactants are generally combined in a mutual solvent such as diethyl ether or benzene. The salt normally precipitates out of solution within about one hour to 10 days and can be isolated by filtration or the solvent can be stripped off by conventional means.

Bases commonly used for formation of salts include ammonium hydroxide and alkali and alkaline earth metal hydroxides, carbonates and bicarbonates, as well as aliphatic and aromatic amines, aliphatic diamines and hydroxy-alkylamines. Bases especially useful in the preparation of addition salts include ammonium hydroxide, potassium carbonate, sodium bicarbonate, calcium hydroxide, methylamine, diethylamine, ethylene diamine, cyclohexylamine and ethanolamine.

The pharmaceutically acceptable salts generally have enhanced solubility characteristics compared to the compound from which they are derived, and thus are often more amenable to formulation as liquids or emulsions.

Pharmaceutical formulations can be prepared by procedures known in the art. For example, the compounds, either alone or in combination with estrogen, can be formulated with common excipients, diluents, or carriers, and formed into tablets, capsules, suspensions, powders, and the like. Examples of excipients, diluents, and carriers that are suitable for such formulations include the following: fillers and extenders such as starch, sugars, mannitol, and silicic derivatives; binding agents such as carboxymethyl cellulose and other cellulose derivatives, alginates, gelatin, and polyvinyl pyrrolidone; moisturizing agents such as glycerol; disintegrating agents such as agaragar, calcium carbonate, and sodium bicarbonate; agents for retarding dissolution such as paraffin; resorption accelerators such as quaternary ammonium compounds; surface active agents such as cetyl alcohol, glycerol monostearate; adsorptive carriers such as kaolin and bentonite; and lubricants such as talc, calcium and magnesium stearate, and solid polyethyl glycols.

The compounds, either alone or in combination with estrogen, can also be formulated as elixirs or solutions for convenient oral administration or as solutions appropriate for parenteral administration, for instance by intramuscular, subcutaneous or intravenous routes. Additionally, the compounds, either alone or in combination with estrogen, can be formulated as sustained release dosage forms and the like. The formulations can be so constituted that they release the active ingredient only or preferably in a particular part of the intestinal tract, possibly over a period of time. The coatings, envelopes, and protective matrices may be made, for example, from polymeric substances or waxes.

The particular dosage of a compound of formula I required to lower serum cholesterol levels will depend upon the severity of the condition, the route of administration, and related factors that will be decided by the attending physician. Generally, accepted and effective daily doses will be from about 0.1 to about 1000 mg., and more typically from about 50 to about 200 mg., although a daily dose of from about 200 to about 600 mg. can also be used. Such dosages will be administered to a patient in need of treatment from once to about three times each day, or more often as needed to effectively lower serum cholesterol levels. Generally, accepted and effective daily doses of estrogen will be from about 0.01 to about 4.0 mg, and more typically from about 0.1 to about 2.0 mg. Such doses are administered to a subject in need of treatment from once to about three times a day, or more often as needed.

The method of the present invention is useful in men, as well as women. The substantial absence of estrogenic response should allow men to benefit from the method of this invention without evidencing the feminizing response of estrogen or estrogen agonists such as gynecomastia. The method of the present invention is especially useful in women, preferably estrogen-deficient women. The estrogen deficiency could occur naturally, such as post-menopausal, or surgically. Patients undergoing or having undergone long-term administration of corticosteroids and those having gonadal dysgenesis may also employ the method of the present invention.

It is usually preferred to administer a compound of formula I in the form of an acid addition salt, as is customary in the administration of pharmaceuticals bearing a basic group, such as the piperidino ring. It is also advantageous to administer such a compound by the oral route to an aging human (e.g. a post-menopausal female).

The following are examples of oral dosage forms useful in this invention. In the formulations, "Active ingredient" means a compound of formula I.

Capsules

Hard gelatin capsules are prepared using one of Formulations 1–5:

| Formulation 1: | |
|---|---|
| Ingredient | Quantity (mg/capsule) |
| Active ingredient | 0.1–1000 |
| Starch, NF | 0–650 |
| Starch flowable powder | 0–650 |
| Silicone fluid 350 centistokes | 0–15 |

The ingredients are blended, passed through a No. 45 mesh U.S. sieve, and filled into hard gelatin capsules.

| Ingredient | Quantity (mg/capsule) |
|---|---|
| Formulation 2: | |
| Raloxifene hydrochloride | 1 |
| Starch, NF | 112 |
| Starch flowable powder | 225.3 |
| Silicone fluid 350 centistokes | 1.7 |
| Formulation 3: | |
| Raloxifene hydrochloride | 5 |
| Starch, NF | 108 |
| Starch flowable powder | 225.3 |
| Silicone fluid 350 centistokes | 1.7 |
| Formulation 4: | |
| Raloxifene hydrochloride | 10 |
| Starch, NF | 103 |
| Starch flowable powder | 225.3 |
| Silicone fluid 350 centistokes | 1.7 |
| Formulation 5: | |
| Raloxifene hydrochloride | 50 |
| Starch, NF | 150 |
| Starch flowable powder | 397 |
| Silicone fluid 350 centistokes | 3.0 |

Tablets

Tablets are prepared using Formulation 6 or 7:

| Formulation 6: | |
|---|---|
| Ingredient | Quantity (mg/tablet) |
| Active ingredient | 0.1–1000 |
| Cellulose, microcrystalline | 0–650 |

-continued

| Formulation 6: | |
|---|---|
| Ingredient | Quantity (mg/tablet) |
| Silicon dioxide, fumed | 0–650 |
| Stearate acid | 0–15 |

The components are blended and compressed to form tablets.

Alternatively, tablets each containing 0.1–1000 mg of active ingredient are made up as follows:

| Formulation 7: | |
|---|---|
| Ingredient | Quantity (mg/tablet) |
| Raloxifene hydrochloride | 0.1–1000 |
| Starch | 45 |
| Cellulose, microcrystalline | 35 |
| Polyvinylpyrrolidone (as 10% solution in water) | 4 |
| Sodium carboxymethyl cellulose | 4.5 |
| Magnesium stearate | 0.5 |
| Talc | 1 |

The active ingredient, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50°–60° C. and passed through a No. 18 mesh U.S. sieve. The sodium carboxymethyl starch, magnesium stearate, and talc, previously passed through a No. 60 U.S. sieve, are then added to the granules which, after mixing, are compressed on a tablet machine to yield tablets.

Suspensions

Suspensions containing 0.1–1000 mg of medicament per 5 mL dose are made as follows:

| Formulation 8: | |
|---|---|
| Ingredient | Quantity (amount/5 mL) |
| Active ingredient | 0.1–1000 mg |
| Sodium carboxymethyl cellulose | 50 mg |
| Syrup | 1.25 mg |
| Benzoic acid solution | 0.10 mL |
| Flavor | q.v. |
| Color | q.v. |
| Purified water | q.s. to 5 mL |

The medicament is passed through a No. 45 mesh U.S. sieve and mixed with the sodium carboxymethyl cellulose and syrup to form a smooth paste. The benzoic acid solution, flavor, and color are diluted with some of the water and added, with stirring. Sufficient water is then added to produce the required volume.

Illustrative compounds of formula I used in the methods of this invention are shown in Table 1:

TABLE 1

| Compound No. | n | R | R$^1$ | R$^2$ | Salt |
|---|---|---|---|---|---|
| 1 | 0 | —OC(O)—C$_6$H$_4$—F | —OC(O)—C$_6$H$_4$—F | piperidino | |
| 2 | 0 | —OC(O)—C$_6$H$_4$—F | —OC(O)—C$_6$H$_4$—F | piperidino | HCl |
| 3 | 0 | —OC(O)—cyclopropyl | —OC(O)—cyclopropyl | piperidino | |
| 4 | 0 | —OC(O)—cyclopropyl | —OC(O)—cyclopropyl | piperidino | HCl |
| 5 | 0 | —OC(O)CH$_2$CH$_2$CH$_3$ | —OC(O)CH$_2$CH$_2$CH$_3$ | piperidino | |
| 6 | 0 | —OC(O)CH$_2$CH$_2$CH$_3$ | —OC(O)CH$_2$CH$_2$CH$_3$ | piperidino | HCl |
| 7 | 0 | —OC(O)C(CH$_3$)$_3$ | —OC(O)C(CH$_3$)$_3$ | piperidino | |
| 8 | 0 | —OC(O)C(CH$_3$)$_3$ | —OC(O)C(CH$_3$)$_3$ | piperidino | HCl |
| 9 | 0 | —OC(O)CH$_2$C(CH$_3$)$_3$ | —OC(O)CH$_2$C(CH$_3$)$_3$ | piperidino | |
| 10 | 0 | —OC(O)CH$_2$C(CH$_3$)$_3$ | —OC(O)CH$_2$C(CH$_3$)$_3$ | piperidino | HCl |
| 11 | 0 | —OC(O)—C$_6$H$_4$—CH$_3$ | —OC(O)—C$_6$H$_4$—CH$_3$ | piperidino | |
| 12 | 0 | —OC(O)—C$_6$H$_4$—CH$_3$ | —OC(O)—C$_6$H$_4$—CH$_3$ | piperidino | HCl |
| 13 | 0 | —OC(O)—C$_6$H$_5$ | —OC(O)—C$_6$H$_5$ | piperidino | |
| 14 | 0 | —OC(O)OCH$_2$CH$_2$CH$_2$CH$_3$ | OC(O)OCH$_2$CH$_2$CH$_2$CH$_3$ | piperidino | |
| 15 | 0 | —OC(O)OCH$_2$CH$_2$CH$_2$CH$_3$ | OC(O)OCH$_2$CH$_2$CH$_2$CH$_3$ | piperidino | HCl |
| 16 | 0 | —OC(O)O—C$_6$H$_5$ | —OC(O)O—C$_6$H$_5$ | piperidino | |
| 17 | 0 | —OC(O)O—C$_6$H$_5$ | —OC(O)O—C$_6$H$_5$ | piperidino | HCl |
| 18 | 0 | —O—C(O)-naphthyl | —O—C(O)-naphthyl | piperidino | |
| 19 | 0 | —OC(O)CH$_2$CH$_2$OCH$_3$ | —OC(O)CH$_2$CH$_2$OCH$_3$ | piperidino | |
| 20 | 0 | —OC(O)CH$_2$CH$_2$OCH$_3$ | —OC(O)CH$_2$CH$_2$OCH$_3$ | piperidino | HCl |
| 21 | 0 | —OH | —OH | piperidino | HCl |
| 22 | 0 | —OH | —OH | piperidino | |
| 23 | 1 | —OH | —OH | piperidino | HCl |
| 24 | 0 | —OH | —OH | pyrrolidino | |
| 25 | 0 | —OH | —OH | pyrrolidino | HCl |
| 26 | 0 | —OH | —OH | hexamethyleneimino | HCl |
| 27 | 0 | —OCH$_3$ | —OCH$_3$ | piperidino | HCl |
| 28 | 0 | —OC(O)CH$_3$ | —OC(O)CH$_3$ | piperidino | HCl |
| 29 | 0 | —OCH$_3$ | H | pyrrolidono | citrate |
| 30 | 0 | —OCH$_3$ | —OCH$_3$ | pyrrolidino | citrate |

TABLE 1-continued

| Compound No. | n | R | R¹ | R² | Salt |
|---|---|---|---|---|---|
| 31 | 0 | —OC(O)—⟨phenyl⟩ | —OC(O)—⟨phenyl⟩ | piperidino | HCl |
| 32 | 0 | —OH | Cl | piperidino | HCl |
| 33 | 0 | —OH | F | piperidino | HCl |

Compounds 1–33 can be prepared as follows:

Preparation 1

Preparation of 6-(4-Fluorobenzoyloxy)-2-[4-(4-fluorobenzoyloxy)phenyl]-benzo[b]thien-3-yl-[4-[2-(piperidin-1-yl)ethoxy]phenyl]-methanone.

Raloxifene, 6-hydroxy-2-(4-hydroxyphenyl)benzo[b]thien-3-yl-[4-[2-(piperidin-1-yl)ethoxy]phenyl]-methanone hydrochloride, (5.1 g, 10 mmol) was suspended in 250 mL of dry tetrahydrofuran (THF) and 7.1 g (70 mmol) of triethylamine, and approximately 10 mg of 4-(N,N-dimethylamino)pyridine were added. The suspension was cooled in an ice bath and placed under an atmosphere of nitrogen. 4-Fluorobenzoyl chloride (4.75 g, 30 mmol), dissolved in 20 mL of dry THF, was slowly added over a twenty minute period. The reaction mixture was stirred and allowed to slowly warm to room temperature over a period of eighteen hours. It was then filtered, and the filtrate was evaporated to a gum in vacuo. The crude product thus obtained was dissolved in a small volume of chloroform and chromotagraphed (HPLC) on a silica gel column eluted with a linear gradient of solvent, starting with chloroform and ending with a mixture of chloroform-methanol (19:1 (v/v)). The fractions containing the desired product as determined by thin layer chromatography (silica, chloroformmethanol (9:1)) were combined and evaporated to a gum. The title compound was crystallized from ether to afford 3.21 g.

PMR: consistent with the structure

FDMS: m/e=717 M+

Elemental Analysis for $C_{42}H_{33}F_2NO_6S$: Theor: C, 70.29; H, 4.60; N, 1.95 Found: C, 70.05; H, 4.60; N, 1.89 Mol. Wt.: 717

Preparation 2

Preparation of 6-(4-Fluorobenzoyloxy)-2-[4-(4-fluorobenzoyloxy)phenyl]-benzo[b]thien-3-yl-[4-[2-(piperidin-1-yl)ethoxy]-phenyl]-methanone hydrochloride.

The compound of Preparation 1 (5.15 g, 7.18 mmol) prepared substantially according to the procedures of Example 1, was dissolved in 25 mL THF, and 150 mL ether was added. Dry HCl gas was bubbled into the solution, and a white gummy precipitate formed. The liquid was removed by decanting, and the residue was crystallized from ethyl acetate with a small amount of ethanol added to effect solution. The product was filtered, washed with ether, and dried to give 4.41 g of the title compound as a white powder.

PMR: consistent with the structure

Elemental Analysis for $C_{42}H_{34}ClF_2NO_6S$: Theor: C, 66.88; H, 4.54; N, 1.86 Found: C, 66.59, H, 4.39; N, 1.60 Mol. Wt.: 753.5

Preparation 3

Preparation of 6-(Cyclopropylcarbonyloxy)-2-[4-(cyclopropylcarbonyloxy)-phenyl]benzo[b]thien-3-yl-[4-[2-(piperidin-1-yl)ethoxy]-phenyl]methanone.

The title compound was prepared substantially according to the procedures of Preparation 1, using cyclopropylcarbonyl chloride, except that the product was not crystallized. Yield=2.27 g.

PMR: consistent with the structure

FDMS: m/e=610 M+

Preparation 4

Preparation of 6-(Cyclopropylcarbonyloxy)-2-[4-(cyclopropylcarbonyloxy)-phenyl]benzo[b]thien-3-yl-[4-[2-(piperidin-1-yl)ethoxy]-phenyl]methanone hydrochloride.

The title compound was prepared from the compound of Preparation 3 substantially as described in Preparation 2.

Preparation 5

Preparation of 6-(n-Butanoyloxy)-2-[4-(n-butanoyloxy)phenyl]benzo[b]thien-3-yl-[4-[2-(piperidin-1-yl)ethoxy]phenyl]methanone.

The title compound was prepared substantially according to the procedures of Preparation 1, using n-butanoyl chloride, to afford 4.12 g of the title compound as an oil.

PMR: consistent with the structure

PDMS: m/e=614 ($M^{+1}$)

Preparation 6

Preparation of 6-(n-Butanoyloxy)-2-[4-(n-butanoyloxy)phenyl]benzo[b]thien-3-yl-[4-[2-(piperidin-1-yl)ethoxy]phenyl]methanone hydrochloride.

The compound of Preparation 5 (4.12 g) was dissolved in ethyl acetate (50 mL), and a solution of HCl in ether was added until the precipitation stopped. The liquid was decanted off, and the white, gummy residue was triturated with diethyl ether and filtered. The residue was dried to afford 1.33 g of the title compound.

PMR: consistent with the structure

Elemental Analysis of for $C_{36}H_{40}ClNO_6S$: Theor.: C, 66.50; H, 6.20; N, 2.15 Found: C, 66.30; H, 6.28; N, 1.98 Mol. Wt.: 650.24

Preparation 7

Preparation of 6-(2,2-Dimethylpropanoyloxy)-2-[4-(2,2-dimethylpropanoyloxy)phenyl]benzo[b]thien-3-yl-[4-[2-(piperidin-1-yl)ethoxy]phenyl]methanone.

The title compound was prepared substantially according to the procedure of Preparation 1, using 2,2-dimethylpropanoyl chloride.

Preparation 8

Preparation of 6-(2,2-Dimethylpropanoyloxy)-2-[4-(2,2-dimethylpropanoyloxy)phenyl]benzo[b]thien-3-yl-[4-[2-(piperidin-1-yl)ethoxy]phenyl]methanone hydrochloride.

The title compound was prepared from the compound of Preparation 7, substantially according to the procedures of Preparation 2.

FDMS: m/e=641 (M-HCl-1)

Elemental Analysis of $C_{38}H_{44}ClNO_6S$: Theor.: C, 67.29; H, 6.54; N, 2.07 Found: C, 67.02; H, 6.54; N, 1.90 Mol. Wt.: 678.29

Preparation 9

Preparation of 6-(3,3-Dimethylbutanoyloxy)-2-[4-(3,3-dimethylbutanoyloxy)-phenyl]benzo[b]thien-3-yl[4-[2-(piperidin-1-yl)ethoxy]-phenyl]methanone.

The title compound was prepared substantially according to the procedures of Preparation 1, using 3,3-dimethylbutanoyl chloride.

Preparation 10

Preparation of 6-(3,3-Dimethylbutanoyloxy)-2-[4-(3,3-dimethylbutanoyloxy)-phenyl]benzo[b]thien-3-yl[4-[2-(piperidin-1-yl)ethoxy]-phenyl]methanone hydrochloride.

The title compound was prepared from the compound of Preparation 9 substantially according to the procedures of Preparation 2.

FDMS: m/e=669 (M-HCl-1)

Elemental Analysis of $C_{40}H_{48}ClNO_6S$: Theor.: C, 68.02; H, 6.85; N, 1.98 Found: C, 67.75; H, 6.83; N, 2.04 Mol. Wt.: 706.35

Preparation 11

Preparation of 6-(4-Methylbenzoyloxy)-2-[4-(4-methylbenzoyloxy)phenyl]benzo[b]thien-3-yl[4-[2-(piperidin-1-yl)ethoxy] phenyl]methanone.

The title compound was prepared substantially according to the procedures described in Preparation 1 using p-toluoyl chloride.

Preparation 12

Preparation of 6-(4-Methylbenzoyloxy)-2-[4-(4-methylbenzoyloxy)phenyl]benzo[b]thien-3-yl[4-[2-(piperidin-1-yl)ethoxy]phenyl]methanone hydrochloride.

The title compound was prepared from its corresponding free base, the compound of Preparation 11, substantially according to the procedures of Preparation 2.

FDMS: m/e=710 (M-HCl-1)

Elemental Analysis of $C_{44}H_{40}ClNO_6S$: Theor.: C, 70.81; H, 5.39; N, 1.88 Found: C, 71.10; H, 5.39; N, 1.94 Mol. Wt.: 746.33

Preparation 13

Preparation of 6-Benzoyloxy-2-[4 -benzoyloxy)phenyl]benzo[b]thien-3-yl[4-[2-(piperidin-1 -yl)ethoxy]-phenyl] methanone.

The title compound was prepared using benzoylchloride substantially according to the procedures of Preparation 1.

FDMS: m/e=682 (M+1)

Elemental Analysis of $C_{42}H_{35}NO_6S$: Calc: C, 73.80; H, 5.14; N, 2.05 Found: C, 73.27; H, 5.27; N, 1.94 Mol. Wt.: 681.8

Preparation 14

Preparation of 6-(n-Butoxycarbonyloxy)-2-[4 (n-butoxycarbonyloxy)phenyl]-benzo[b]thien-3-yl[4-[2-(piperidin-1-yl)ethoxy]-phenyl]methanone.

The title compound was prepared substantially according to the procedures of Preparation 1 using n-butylchloroformate. Yield=6.13 g as an oil.

PMR: consistent with structure

FDMS: m/e=674 (M+1)

Preparation 15

Preparation of 6-(n-Butoxycarbonyloxy)-2-[4 (n-butoxycarbonyloxy)phenyl]-benzo[b]thien-3-yl[4-[2-(piperidin-1-yl)ethoxy]phenyl]-methanone hydrochloride.

The compound of P 14 was converted to the corresponding hydrochloride salt substantially according to the procedures of Preparation 6.

PMR: consistent with structure

Elemental Analysis of $C_{38}H_{44}ClNO_8S$: Calc: C, 64.26; H, 6.24; N, 1.97 Found: C, 63.97; H, 6.34; N, 1.98 Mol. Wt.: 710.29

Preparation 16

Preparation of 6-(Phenoxycarbonyloxy)-2 -[4(phenoxycarbonyloxy)phenyl]-benzo[b]thien-3-yl[4-[2 -(piperidin-1-yl)ethoxy]phenyl]-methanone.

The title compound was prepared substantially according to the procedures of Preparation 1, using phenyl chloroformate. Yield=3.59 g as a tan amorphous powder.

PMR: consistent with structure

FDMS: m/e=713 (M+)

Preparation 17

Preparation of 6-(Phenoxycarbonyloxy)-2 -[4(phenoxycarbonyloxy)phenyl]-benzo[b]thien-3-yl[4-[2 -(piperidin-1-yl)ethoxy]phenyl]-methanone hydrochloride.

The compound of Preparation 16 was converted to the corresponding hydrochloride salt substantially according to the procedures described in Preparation 6.

PMR: consistent with structure

Elemental Analysis of $C_{38}H_{44}ClNO_8S$: Calc: C, 67.24; H, 4.84; N, 1.87 Found: C, 66.94; H, 4.96; N, 1.84 Mol. Wt.: 750.27

Preparation 18

Preparation of 6-(1-Naphthoyloxy)-2-[4(1 -naphthoyloxy)phenyl]benzo[b]thien-3-yl[4-[2-(piperidin-1 -yl)ethoxy] phenyl]methanone.

The title compound was prepared substantially according to the procedures of Preparation 1 using 1-naphthoylchloride. Yield=3.5 g of a white amorphous powder PMR: consistent with structure FDMS: m/e=781 (M+)

Elemental Analysis of $C_{50}H_{39}NO_6S$: Calc: C, 76.80; H, 5.03; N, 1.79 Found: C, 76.53; H, 5.20; N, 1.53 Mol. Wt.: 781.94

Preparation 19

Preparation of 6-(Methoxypropanoyloxy)-2 -[4(methoxypropanoyloxy)phenyl]-benzo[b]thien-3-yl[4-[2 -(piperidin-1-yl)ethoxy]phenyl]-methanone.

The title compound was prepared substantially according to the procedures of Preparation 1 using 3-methoxypropionyl chloride prepared from the corresponding 3-methoxypropionic acid by conventional procedures. Yield=3.61 g of a gummy solid.

PMR: consistent with structure

FDMS: m/e=618 (M+1)

Preparation 20

Preparation of 6-(Methoxypropanoyloxy)-2 -[4(methoxypropanoyloxy)phenyl]-benzo[b]thien-3-yl[4-[2 -(piperidin-1-yl)ethoxy]phenyl]-methanone hydrochloride.

The title compound was prepared from 3.5 g of the compound of Preparation 19 by substantially the same procedures as Preparation 2. Yield=1.65 g of amorphous white powder.
PMR: consistent with structure
FDMS: m/e=618 (M+1)
Elemental Analysis of $C_{34}H_{36}NO_8S$: Calc: C, 62.43; H, 5.55; N, 2.14 Found: C, 62.23; H, 5.63; N, 2.15

Preparation 21

Preparation of 6-hydroxy-2-(4-hydroxyphenyl)-3[4-(2 -piperidinoethoxy)benzoyl]-benzo[b]thiophene hydrochloride.

The title compound was prepared by substantially the same procedures as Preparation 8 of U.S. Pat. No. 4,418,068.
NMR: consistent with proposed structure MS: m/e=474 (M+-HCl) pkg=8.0, 11.6, & 12.2 (66% DMF) Elemental Analysis of $C_{28}H_{28}ClNO_4$ Calc: C, 65.94; H, 5.53; N, 2.75 Found: C, 65.93; H, 5.50; N, 2.82 MW=510.06

Preparation 22

Preparation of 6-hydroxy-2-(4-hydroxyphenyl)-3[4-(2 -piperidinoethoxy)benzoyl]-benzo[b]thiophene.

The title compound was prepared by substantially the same procedures as Example 3 of U.S. Pat. No. 4,418,068.

Preparation 23

Preparation of 6-hydroxy-2-(4-hydroxyphenyl)-3-[4-(3 -piperindinopropoxy)benzoyl]benzo[b]thiophene hydrochloride.

The title compound was prepared by substantially the same procedures as Example 17 of U.S. Pat. No. 4,418,068 using 4-(3-piperidinopropyloxy)benzoic acid hydrochloride which was prepared by substantially the same procedures shown in Jones et al., *J. Med. Chem.*, 27(8) 1057–1066, 1064 (1984) using N-(3 -chloropropyl)piperidine.

NMR and $C^{13}MR$ were consistent with proposed structure MS: m/e=487 (M+-HCl) F.D IR: 3548, 3391, 3181, 1597 $CM^{-1}$ (KBr) Elemental Analysis Calc: C, 66.46; H, 5.77; N, 2.67; Cl, 6.76; S, 6.12 Found: C, 65.96; H, 6.32; N, 2.68; Cl, 6.46; S, 6.07 $C_{29}H_{30}$ Cl N $O_{21}$ S MW=524.08

Preparation 24

Preparation of 6-hydroxy-2-(4-hydroxyphenyl)-3-[4-(2 -pyrrolidinoethoxy)benzoyl]benzo[b]thiophene.

The title compound was prepared using 4-(2-pyrrolidinoethoxy)benzoic acid by substantially following the procedures of Example 17 of U.S. Pat. No. 4,418,068.

Preparation 25

Preparation of 6-hydroxy-2-(4-hydroxyphenyl)-3-[4-(2 -pyrrolidinoethoxy)benzoyl]benzo[b]thiophene hydrochloride.

The title compound was prepared from the compound of Preparation 24 by substantially following the procedures of Preparation 6.

Elemental Analysis for $C_{27}H_{26}ClNO_4S$ PMR and $C^{13}MR$ were consistent with the proposed structure. MS: m/e=460 (M$^+$-HCl) (FD) Calc: C, 65.38; H, 5.28; N, 2.82; Cl, 7.15; S, 6.46 Found: C,65.10; H, 5.48; N, 2.82; Cl, 6.91; S, 6.24 MW=496.03

Preparation 26

Preparation of 6-hydroxy-2-(4-hydroxyphenyl)-3-[4-(2 -hexamethyleneiminoethoxy)benzoyl]benzo[b]thiophene hydrochloride.

The title compound was prepared using 4-(2 -hexamethylaminodroxy)benzoic acid by substantially following the procedures of Examples 1–7 of U.S. Pat. No. 4,418,068. 4-(2 -hexamethylaminoethoxy)benzoic acid was prepared by substantially following the procedures of Jones et al., *J. Med. Chem.* 27 (8), 1057–1066, 1064 (1984) using N-(2-chlorethyl)hexamethylacimine.

PMR and $C^{13}MR$ were consistent with proposed structure. MS m/e=488 (M-HCl) FAB Elemental Analysis: Calc: C, 66.46; H, 5.77; N,2.67; Cl, 6.76; S, 6.12 Found: C, 58.71; H, 5.58; N, 2.30; Cl, 7.19; S, 6.07

Preparation 27

Preparation of 6-methoxy-2-(4-methoxyphenyl)-3-[4-(2 -piperidinoethoxy)benzoyl]benzo[b]thiophene hydrochloride.

The title compound was prepared by substantially following the procedures of Preparation H of U.S. Pat. No. 4,418,068 and Preparation 6.

PMR was consistent with proposed structure. MS m/e= 502 (M-HCl) FD Elemental Analysis: Calc: C, 66.96; H, 5.99; N,2.60; Cl, 6.59 Found: C, 66.93; H, 6.17; N, 2.62; Cl, 6.68

Preparation 28

Preparation of 6-acetoxy-2-(4-acetoxyphenyl)-3-[4-(2 -piperidinoethoxy)benzoyl]benxo[b]thiophene hydrochloride.

The title compound was prepared by substantially following the procedures of Example 1 of U.S. Pat. No. 4,418,068.

Preparation 29

Preparation of 2-phenyl-3-[4-(2-pyrrolidinoethoxy)benzoyl] -6 -methoxybenzothiophene citrate.

The title compound was prepared by substantially following the procedures of Example 12 of U.S. Pat. No. 4,133, 814.

Preparation 30

Preparation of 2-(4-methoxyphenyl)-3-[4-(2 -pyrrolidinoethoxy)benzoyl]-6-methoxybenzothiophene citrate.

The title compound was prepared by substantially following the procedures of Example 30 of U.S. Pat. No. 4,133, 814.

Preparation 31

Preparation of 6-Benzoyloxy-2-[4 -benzoyloxy)phenyl] benzo[b]thien-3-yl[4-[2-(piperidin-1 -yl)ethoxy]-phenyl] methanone hydrochloride.

The title compound was prepared from the compound of Preparation 13 substantially as described in Preparation 6.

The following nonlimiting test examples illustrate the methods of this invention.

Preparation 32

Preparation of [2-(4-chlorophenyl)-6-hydroxy-benzo[b] thien-3 yl]-[4-[2-(piperidin-1-yl)ethoxy]phenyl]methanone hydrochloride.

[6-methoxy-2-(4-chlorophenyl)benzo[b]thien-3-yl][4-[2-(piperidin-1-yl)ethoxy]phenyl]methanone (6.7 g) was dissolved in dichloromethane. AlCl$_3$ (5.3 g) was added to this solution. Ethanethiol (5.0 g, 5.9 mL) was added all at once, and the dark red solution was stirred overnight. The solution was then poured slowly onto ice (ca. 400 mL). The organic phase was separated from the aqueous phase, and the aqueous phase was extracted with chloroform. The chloroform extract was evaporated to give a yellow residue which was redissolved in ethyl acetate. The ethyl acetate solution was washed with sat NaHCO$_3$, water and brine. The solution was then dried over NaSO$_4$ and evaporated to give a yellow amorphous solid. Yield: 5.1 g (crude).

The crude material was chromatographed over silica gel (Waters Prep 500 system), eluting with MeOH:CHCl$_3$ (1:9). Fractions of 300 mL were collected. Fractions containing the product were combined and evaporated to give the title compound base as a yellow solid.

The hydrochloride salt was formed by dissolving the yellow solid in dry tetrahydrofuran and bubbling anhydrous HCl into the solution. The solution was evaporated to give a yellow-brown material. This material was crystallized from acetone to give the title compound as small white crystals. Yield: 2.2 g.

Analysis: Calc'd: C, 63.63; H, 5.15; N, 2.65; S, 6.07; Cl, 13.42. Found: C, 63.53; H, 5.15; N, 2.51; S, 5.58; Cl, 13.23. M.P.: 223°–224.5° C.

Preparation 33

Preparation of [2-(4-fluorophenyl)-6-hydroxy-benzo[b]thien-3-yl]-[4-[2-(piperidin-1-yl)ethoxy]phenyl]methanone hydrochloride.

The title compound was prepared using procedures like those described in Preparation 32 with the corresponding appropriate starting material.

Test Procedure

In the examples illustrating the methods, a post-menopausal model was used in which effects of different treatments upon circulating lipids were determined.

Seventy-five day old female Sprague Dawley rats (weight range of 200 to 225 g) were obtained from Charles River Laboratories (Portage, Mich.). The animals were either bilaterally ovariectomized (OVX) or exposed to a Sham surgical procedure at Charles River Laboratories, and then shipped after one week. Upon arrival, they were housed in metal hanging cages in groups of 3 or 4 per cage and had ad libitum access to food (calcium content approximately 0.5%) and water for one week. Room temperature was maintained at 22.2°±1.7° C. with a minimum relative humidity of 40%. The photoperiod in the room was 12 hours light and 12 hours dark.

Dosing Regimen/Tissue Collection.

After a one week acclimation period (therefore, two weeks post-OVX) daily dosing with test compound was initiated. All compounds were administered orally at 1 ml/kg body weight unless otherwise stated. 17β-Estradiol was administered subcutaneously in a 20% polyethylene glycol vehicle: 17α-ethynyl estradiol and the test compound were given orally, unless otherwise stated, as a suspension in 1% carboxymethylcellulose or 20% cyclodextrin. Animals were dosed daily for 4 days. Following the dosing regimen animals were weighed and anesthetized with a ketamine: Xylazine (2:1, V:V) mixture, and a blood sample was collected by cardiac puncture. Each animal was then sacrificed by asphyxiation with CO$_2$; the uterus was removed through a midline incision and a wet weight was determined.

Cholestrol Analysis.

Blood samples were allowed to clot at room temperature for 2 hrs, and serum was obtained following centrifugation for 10 min at 3000 rpm. Serum cholesterol was determined using a Boehringer Mannheim Diagnostics high performance cholesterol assay. Briefly, the cholesterol was oxidized to cholest-4-en-3-one and hydrogen peroxide. The hydrogen peroxide was then reacted with phenol and 4-aminophenazone in the presence of peroxidase to produce a p-quinone imine dye, which was read spectrophotometrically at 500 nm. Cholesterol concentration was then calculated against a standard curve. The entire assay was automated using a Biomek Automated Workstation.

Uterine Eosinophil Peroxidase (EPO) Assay.

Uteri were kept at 4° C. until time of enzymatic analysis. The uteri were then homogenized in 50 volumes of 50 mM Tris buffer (pH -8.0) containing 0.005% Triton X-100. Upon addition of 0.01% hydrogen peroxide and 10 mM o-phenylenediamine (final concentrations) in Tris buffer, increase in absorbance was monitored for one minute at 450 nm. The presence of eosinophils in the uterus is an indication of estrogenic activity of a compound. The maximal velocity of a 15 second interval was determined over the initial, linear portion of the reaction curve.

Sources of Compounds:

17β-estradiol, 17α-ethynyl estradiol and tamoxifen were obtained from Sigma Chemical Co., St. Louis, Mo.

Experimental Groups:

All experimental groups were comprised of five or six animals.

INFLUENCE OF RALOXIFENE ON SERUM CHOLESTEROL

The results of control treatments are presented in Table 1. In summary, ovariectomy of the rats caused an increase in serum cholesterol as compared to intact vehicle treated controls. Estrogen, administered in the orally active form of ethynyl estradiol (EE$_2$), caused a decrease in serum cholesterol in a dose dependent manner, but it also exerted a stimulatory action on the uterus resulting in uterine weights approaching that of an intact rat when administered at 100 μg/kg/day. Results are reported as the mean of measurements from 5 to 6 rats±the standard error of the mean.

TABLE 1

| | Serum Cholesterol (mg/dL) | Uterine Weight Ratio (mg uterus/g body weight) | EPO Activity (m OD/min) |
|---|---|---|---|
| Ovariectomy control (0.3 mL CMC) | 81.3 ± 13.4 | 0.48 ± 0.04 | 5 ± 2 |
| Intact control (0.3 mL CMC) | 72.6 ± 14.6 | 1.70 ± 0.12 | 216 ± 32 |
| EE$_2$ 0.1 mg/kg | 46.5 ± 5.8 | 1.45 ± 0.08 | 366 ± 17 |

In these studies, raloxifene also caused a serum cholesterol decrease in a dose dependent manner; however, only minimal increase of uterine weight over the ovariectomized controls was present in these animals. The effects of raloxifene are represented in Table 2. Accordingly, each point reflects the responses of 5 to 6 rats and depicts a typical dose response curve for raloxifene in this model. Results are reported as the mean±the standard error of the mean.

TABLE 2

|  | Serum Cholesterol (mg/dL) | Uterine Weight Ratio (mg uterus/g body weight) | EPO Activity (m OD/min) |
|---|---|---|---|
| Ovariectomy control (0.3 mL CMC) | 87.5 ± 8.1 | 0.45 ± 0.02 | 4.8 ± 1.6 |
| $EE_2$ 0.1 mg/kg | 8.1 ± 1.6 | 1.01 ± 0.03 | 295.1 ± 32.5 |
| raloxifene 0.01 mg/kg | 57.5 ± 6.9 | 0.54 ± 0.04 | 6.6 ± 1.4 |
| raloxifene 0.10 mg/kg | 35.3 ± 3.2 | 0.54 ± 0.04 | 5.8 ± 0.6 |
| raloxifene 1.00 mg/kg | 31.6 ± 3.4 | 0.56 ± 0.04 | 7.2 ± 2.0 |

Raloxifene was administered alone or in combination with 17β-estradiol. Rats treated with raloxifene alone had uterine weights which were marginally higher than the ovariectomized controls and much less than those of 17β-estradiol treated rats, which approached those of the intact controls. Conversely, raloxifene treatment substantially reduced serum cholesterol in ovariectomized rats. When given in combination with 17β-estradiol, the 17β-estradiol did not appreciably reduce the effects of raloxifene on serum cholesterol. The results are shown in Table 3.

TABLE 3

| Experiment A | Serum Cholesterol (mg/dL) | Uterine Weight Ratio (mg uterus/g body weight) | EPO Activity (m OD/min) |
|---|---|---|---|
| Ovariectomy control (0.3 mL CMC) | 47.8 ± 8.2 | 0.62 ± 0.04 | 8 ± 2 |
| Intact control (0.3 mL CMC) | 48.6 ± 7.3 | 2.25 ± 0.14 | 245 ± 27 |
| 17 β-estradiol 0.1 mg/kg | 39.6 ± 4.6 | 1.41 ± 0.04 | 403 ± 55 |
| 17 β-estradiol 0.1 mg/kg + raloxifene 10 mg/kg | 19.3 ± 4.3 | 0.99 ± 0.04 | 83 ± 31 |
| raloxifene 10 mg/kg | 25.6 ± 7.1 | 0.68 ± 0.04 | 2 ± 1 |

The ability of raloxifene to lower serum cholesterol was compared to that of tamoxifen (SIGMA, St. Louis, Mo.). Tamoxifen, a well known antiestrogen currently used in the treatment of certain cancers, has been shown to lower serum cholesterol (see for example, Love, R., et al., *J. Nat. Can. Inst.*, 82, 1327–1332 (1990). A range of doses of raloxifene and tamoxifen was administered orally to ovariectomized rats as in the previous evaluation. Although both of these agents displayed the ability to lower serum cholesterol while evoking only modest uterotrophic activity, as identified by gains in uterine weight, a comparison of several histological parameters demonstrated a marked difference between the rats treated with these agents. The data are set forth in Tables 4 and 5, below.

Increases in epithelial height are a sign of estrogenicity of therapeutic agents and may be associated with increased incidence of uterine cancer. When raloxifene was administered as described above, there was no statistically measurable increase in epithelial height over the ovariectomized controls. This was in contrast to the results seen with tamoxifen and estrogen. At all doses given, tamoxifen increased epithelial height equal to that of an intact rat. Estradiol treatment increased epithelial height to a thickness greater than intact rats.

Estrogenicity was also assessed by evaluating the adverse response of eosinophil infiltration into the uterus. Raloxifene did not cause any increase in the number of eosinophils observed in the stromal layer of ovariectomized rats while tamoxifen caused a substantial increase in the response. Estradiol, as expected, caused a large increase in eosinophil infiltration.

Little or no difference was detectable between raloxifene and tamoxifen effects on thickness of the stroma and myometrium. Both agents caused an increase in these measurements that was much less than the effect of estrogen.

A total score of estrogenicity, which was a compilation of all four parameters, showed that raloxifene was substantially less estrogenic than tamoxifen,

TABLE 4

|  | Serum Cholesterol (mg/dL) | Uterine Weight Ratio (mg uterus/g body weight) | EPO Activity (m OD/min) |
|---|---|---|---|
| Ovariectomy control (0.3 mL CMC) | 61.4 ± 3.6 | 0.42 ± 0.05 | 4.3 ± 0.2 |
| $EE_2$ 100 µg/kg | 9.1 ± 2.0 | 0.93 ± 0.08 | 155.6 ± 45.4 |
| raloxifene 1 mg/kg | 35.8 ± 4.1 | 0.54 ± 0.03 | 5.0 ± 0.6 |
| tamoxifen 1 mg/kg | 36.5 ± 2.8 | 0.76 ± 0.04 | 130.4 ± 31.4 |

TABLE 5

|  | Epithelial Height | Stromal Eosinophilis | Myometrial Thickness | Stromal Expansion |
|---|---|---|---|---|
| Ovariectomy control (0.3 mL CMC) | 1.24 | 1.00 | 4.42 | 10.83 |
| Intact control (0.3 mL CMC) | 2.71 | 4.17 | 8.67 | 20.67 |
| $EE_2$ 100 µg/kg | 3.42 | 5.17 | 8.92 | 21.17 |
| raloxifene 1 mg/kg (subcutaneously) | 1.67 | 1.17 | 5.42 | 14.00 |
| tamoxifen 1 mg/kg (subcutaneously) | 2.58 | 2.83 | 5.50 | 14.17 |

Other compounds of formula I were administered orally in the rat assay described supra. Table 6 reports the effect of a 1 mg/kg dose of several compounds in terms of a percent decrease of serum cholesterol, percent uterine weight increase and EPO activity; and Table 7 reports the effects of varying doses of Compounds 32 and 33 in these assays.

TABLE 6

| Compound Number | % Decrease of Serum Cholesterol[a] | % Uterine Weight Gain[b] | EPO Activity (m OD/min)[c] |
|---|---|---|---|
| 8 | 64.4 | 49.2 | 9.1 |
| 10 | 71.9 | 45.3 | 4.3 |
| 12 | 75.6 | 41.6 | 4.6 |
| 13 | 69.7 | 35.9 | 5.5 |
| 16 | 80.2 | 43.9 | 3.1 |
| 17 | 55.2 | 7.1 | 8.2 |
| 22 | 75.6 | 38.1 | 4.6 |
| 23 | 49.5 | 87.5 | 16.3 |
| 24 | 73.0 | 48.9 | 9.5 |
| 25 | 81.6 | 10.6 | 16.4 |
| 26 | 64.1 | 53.8 | 5.6 |
| 27 | 32.9 | 58.0 | — |
| 30 | 15.6 | 4.5 | 1.9 |
| 31 | 68.0 | 38.6 | 5.2 |

[a]Percent decrease of serum cholesterol equals (serum cholesterol of treated OVX animals minus serum cholesterol of untreated OVX animals) divided by (serum cholesterol of OVX animals) multiplied by 100%.
[b]Percent uterine weight gain equals (uterine weight of treated OVX animals minus uterine weight of OVX animals) divided by (uterine weight of OVX animals) multiplied by 100%.
[c]Vmax for eosinophil peroxidase activity.

TABLE 7

Comparison of Compounds 32-33 with Estradiol

| Compound | Dose (mg/kg) | % Decrease of Serum Cholesterol[a] | % Uterine Weight Increase over OVX[b] | Uterine EPO Activity (m OD/min)[3] |
|---|---|---|---|---|
| EE2 | 0.1 | 89.7 | 164.1 | 144.5 |
| 32 | 0.1 | 32.3 | 56.6 | 8 |
| 32 | 1 | 69.9 | 46.3 | 8.8 |
| 32 | 10 | 65.0 | 39.0 | 6 |
| 33 | 0.1 | 33.8 | 10.9 | 3.5 |
| 33 | 1 | 46.0 | 37.7 | 11.4 |
| 33 | 10 | 41.3 | 66.8 | 8.9 |

[a]Percent decrease of serum cholesterol equals (serum cholesterol of treated OVX animals minus serum cholesterol of untreated OVX animals) divided by (serum cholesterol of OVX animals) multiplied by 100%.
[b]Percent uterine weight gain equals (uterine weight of treated OVX animals minus uterine weight of OVX animals) divided by (uterine weight of OVX animals) multiplied by 100%.
[c]Vmax for eosinophil peroxidase activity.

We claim:

1. A method of lowering serum cholesterol levels comprising administering to a patient a serum cholesterol lowering amount of a compound having the formula

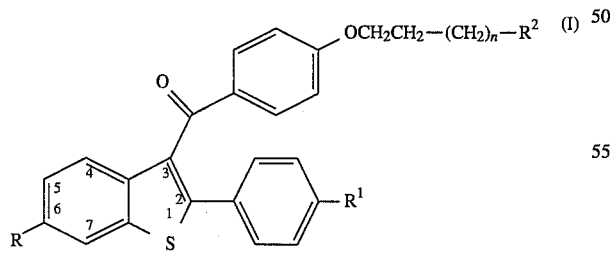

wherein n is 0, 1 or 2;

R is hydroxyl, methoxy, $C_1$–$C_7$ alkanoyloxy, $C_3$–$C_7$ cycloalkanoyloxy, ($C_1$–$C_6$ alkoxy)-$C_1$–$C_7$ alkanoyloxy, substituted or unsubstituted aroyloxy, or substituted or unsubstituted aryloxycarbonyloxy;

$R^1$ is hydrogen, hydroxyl, halo, methoxy, $C_1$–$C_7$ alkanoyloxy, $C_3$–$C_7$ cycloalkanoyloxy, ($C_1$–$C_6$ alkoxy)-$C_1$–$C_7$ alkanoyloxy, substituted or unsubstituted aroyloxy, or substituted or unsubstituted aryloxycarbonyloxy;

$R^2$ is a heterocyclic ring selected from the group consisting of pyrrolidino, piperidino, or hexamethyleneimino; or a pharmaceutically acceptable salt on solvate thereof.

2. A method of claim 1 wherein the patient is a female.

3. A method of claim 2 wherein the female is estrogen deficient.

4. A method of claim 3 wherein the female is postmenopausal.

5. A method of claim 4 wherein:

n is 0;

R and $R^1$ are independently hydroxyl, $C_1$–$C_7$ alkanoyloxy, ($C_1$–$C_6$ alkoxy)-$C_1$–$C_7$ alkanoyloxy, unsubstitued or substituted benzoyloxy or unsubstituted or substituted phenoxycarbonyloxy; and $R^2$ is piperidino or pyrrolidino; or a pharmaceutically acceptable salt or solvate thereof.

6. A method of claim 5 wherein:

R and $R^1$ are the same and are selected from hydroxyl, $C_1$–$C_7$ alkanoyloxy, or ($C_1$–$C_6$ alkoxy)-$C_1$–$C_7$ alkanoyloxy; or a pharmaceutically acceptable salt or solvate thereof.

7. A method of claim 6 wherein:

R and $R^1$ are hydroxyl; or a pharmaceutically acceptable salt or solvate thereof.

8. A method of claim 7 wherein the compound is 6-hydroxy-2-(4-hydroxyphenyl)benzo[b]thien-3-yl-4-[2-(piperidin-1-yl)ethoxyphenyl]methanone or a pharmaceutically acceptable salt or solvate thereof.

9. A method of claim 7 wherein the compound is 6-hydroxy-2-(4-hydroxyphenyl)benzo[b]thien-3-yl-4-[2-(1-pyrrolidino)ethoxyphenyl]methanone or a pharmaceutically acceptable salt or solvate thereof.

10. A method of claim 8 wherein the compound is 6-hydroxy-2-(4-hydroxyphenyl)benzo[b]thien-3-yl-4-[2-(piperidin-1-yl)ethoxyphenyl]methanone hydrochloride.

11. A method of claim 9 wherein the compound is 6-hydroxy-2-(4-hydroxyphenyl)benzo[b]thien-3-yl-4-[2-(1-pyrrolidino)ethoxyphenyl]methanone hydrochloride.

12. A method of lowering serum cholesterol levels comprising administering estrogen and a compound having the formula

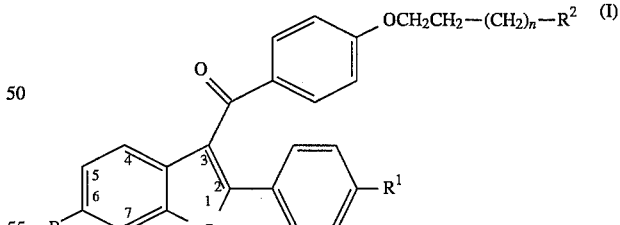

wherein n is 0, 1 or 2;

R is hydroxyl, methoxy, $C_1$–$C_7$ alkanoyloxy, $C_3$–$C_7$ cycloalkanoyloxy, ($C_1$–$C_6$ alkoxy)-$C_1$–$C_7$ alkanoyloxy, substituted or unsubstituted aroyloxy, or substituted or unsubstituted aryloxycarbonyloxy;

$R^1$ is hydrogen, hydroxyl, chloro, bromo, methoxy, $C_1$–$C_7$ alkanoyloxy, $C_3$–$C_7$ cycloalkanoyloxy, ($C_1$–$C_6$ alkoxy)-$C_1$–$C_7$ alkanoyloxy, substituted or unsubstituted or aroyloxy, or substituted or unsubstituted aryloxycarbonyloxy;

$R^2$ is a heterocyclic ring selected from the group consisting of pyrrolidino, piperidino, or hexamethyleneimino; or a pharmaceutically acceptable salt or solvate thereof; to a patient in a combination that lowers the patient's serum cholesterol level.

13. A method of claim 12 wherein the patient is a female.

14. A method of claim 13 wherein the female is estrogen deficient.

15. A method of claim 14 wherein the female is postmenopausal.

16. A method of claim 15 wherein:

n is 0;

R and $R^1$ are independently hydroxyl, $C_1$–$C_7$ alkanoyloxy, ($C_1$–$C_6$ alkoxy)-$C_1$–$C_7$ alkanoyloxy, unsubstituted or substituted benzoyloxy or unsubstituted or substituted phenoxycarbonyloxy; and $R^2$ is piperidino or pyrrolidino; or a pharmaceutically acceptable salt or solvate thereof.

17. A method of claim 16 wherein:

R and $R^1$ are the same and are selected from hydroxyl, $C_1$–$C_7$ alkanoyloxy, or ($C_1$–$C_6$ alkoxy)-$C_1$–$C_7$ alkanoyloxy; or a pharmaceutically acceptable salt or solvate thereof.

18. A method of claim 17 wherein:

R and $R^1$ are hydroxyl; or a pharmaceutically acceptable salt or solvate thereof.

19. A method of claim 18 wherein the compound is 6-hydroxy-2-(4-hydroxyphenyl)benzo[b]thien-3-yl-4-[2-(piperidin-1-yl)ethoxyphenyl]methanone or a pharmaceutically acceptable salt or solvate thereof.

20. A method of claim 18 wherein the compound is 6-hydroxy-2-(4-hydroxyphenyl)benzo[b]thien-3-yl-4-[2-(1-pyrrolidino)ethoxyphenyl]methanone or a pharmaceutically acceptable salt or solvate thereof.

21. A method of claim 19 wherein the compound is 6-hydroxy-2-(4-hydroxyphenyl)benzo[b]thien-3-yl-4-[2-(piperidin-1-yl)ethoxyphenyl]methanone hydrochloride.

22. A method of claim 20 wherein the compound is 6-hydroxy-2-(4-hydroxyphenyl)benzo[b]thien-3-yl-4-[2-(1-pyrrolidino)ethoxyphenyl]methanone hydrochloride.

* * * * *

UNITED STATES PATENT AND TRADEMARK OFFICE
CERTIFICATE OF CORRECTION

PATENT NO. : 5,464,845　　　　　　　　　　　　　　　Page 1 of 2
DATED　　　 : November 7, 1995
INVENTOR(S) : Larry J. Black, et al It is certified that error appears in the above-indentified patent and that said Letters Patent is hereby corrected as shown below:

Column 4, line 31, delete "ringselected" and insert therfor --ring selected--.

Column 5, line 19, delete "infra" and insert therefor --*infra*--.

Column 7, line 17, delete "functionatities" and insert therfor --functionalities--.

Column 7, line 43, delete "subcrate" and insert therefor --suberate--.

Column 13, line 31, delete "in vacuo" and insert therfor --*in vacuo*--.

Column 14, line 37, delete "PDMS:" and insert therefor --PDMS:--.

Column 15, line 36, delete "p-toluoyl" and insert therfor --p-toluoyl--.

Column 18, line 66, delete "thien-3 yl]-" and insert therefor --thien-3-yl]--.

Column 19, lines 49-50, delete "ad libitum" and insert therfor --*ad libitum*--.

Column 20, line 46, delete "rats±the" and insert therefor --rats ± the--.

UNITED STATES PATENT AND TRADEMARK OFFICE
CERTIFICATE OF CORRECTION

PATENT NO. : 5,464,845

DATED : November 7, 1995

INVENTOR(S) : Larry J. Black, et al

It is certified that error appears in the above-indentified patent and that said Letters Patent is hereby corrected as shown below:

Column 21, line 1, delete "mean±the" and insert therefor --mean ± the--.

Column 22, line 60, delete "supra." and insert therefor --$\underline{supra}$.--.

Column 23, line 31, delete "(m OD/min)$^3$" and insert therefor --m (OD/min)$^c$--.

Signed and Sealed this

Fourth Day of June, 1996

*Attest:*

BRUCE LEHMAN

*Attesting Officer*  *Commissioner of Patents and Trademarks*